(12) United States Patent
Klippel

(10) Patent No.: US 8,032,396 B2
(45) Date of Patent: Oct. 4, 2011

(54) SYSTEM AND METHOD FOR OFFERING AND GUARANTEEING RENEWAL OF SUSPENDABLE HEALTHCARE BENEFITS

(75) Inventor: Charles Klippel, Avon, CT (US)

(73) Assignee: Aetna Inc., Hartford, CT (US)

( * ) Notice: Subject to any disclaimer, the term of this patent is extended or adjusted under 35 U.S.C. 154(b) by 1197 days.

(21) Appl. No.: 11/534,974

(22) Filed: Sep. 25, 2006

(65) Prior Publication Data
US 2008/0077450 A1    Mar. 27, 2008

(51) Int. Cl.
*G06Q 10/00*    (2006.01)
(52) U.S. Cl. .................................. 705/3; 705/2
(58) Field of Classification Search ............ 705/2, 3
See application file for complete search history.

(56) References Cited

U.S. PATENT DOCUMENTS

| | | | |
|---|---|---|---|
| 4,632,428 A | 12/1986 | Brown | |
| 5,235,507 A | 8/1993 | Sackler et al. | |
| 5,832,447 A | 11/1998 | Ricker et al. | |
| 6,343,271 B1 | 1/2002 | Peterson et al. | |
| 7,124,088 B2* | 10/2006 | Bauer et al. | 705/4 |
| 7,392,201 B1* | 6/2008 | Binns et al. | 705/4 |
| 2002/0022982 A1* | 2/2002 | Cooperstone et al. | 705/7 |
| 2002/0156657 A1* | 10/2002 | de Grosz et al. | 705/4 |
| 2003/0083906 A1 | 5/2003 | Howell et al. | |
| 2005/0288970 A1* | 12/2005 | Holcom et al. | 705/4 |
| 2006/0200368 A1* | 9/2006 | Casey | 705/3 |
| 2006/0265255 A1 | 11/2006 | Williams | |
| 2007/0038484 A1 | 2/2007 | Hoffner et al. | |
| 2007/0239492 A1* | 10/2007 | Sweetland et al. | 705/4 |

OTHER PUBLICATIONS http://www.opm.gov/fedregis/2002/66-0041305-a.pdf.*
http://www.umsystem.edu/ums/departments/hr/benefits/military.shtml#.*

* cited by examiner

*Primary Examiner* — Robert Morgan
*Assistant Examiner* — Maroun Kanaan
(74) *Attorney, Agent, or Firm* — Leydig, Voit & Mayer, Ltd.

(57) ABSTRACT

A system and method are described whereby a healthcare consumer purchases a suspendable plan while having group coverage and is able to suspend the benefits until group coverage becomes unavailable. When group coverage is not desired or is not available, the consumer can activate the benefits under the suspendable plan. Similarly, a healthcare consumer can buy a suspendable plan while not covered by a group plan and activate the benefits under the plan when not employed. The health plan organization, in turn, guarantees renewal of one or more benefits suspended under the plan throughout the life of the policy at the underwriting status determined when the consumer initially applied for suspendable coverage and, most likely, was in better health. When the consumer chooses to suspend one or more benefits under the plan, the healthcare plan organization reduces the plan premium to a residual premium reflecting the risk associated with providing a renewal guarantee.

20 Claims, 8 Drawing Sheets

| | | |
|---|---|---|
| | Fixed Residual Premium: | 10% |
| Optional Benefit Suspension Feature | Select Excess Premium Allocation (after payment of fixed residual premium above) | |
| Premium Reduction | | 90% |
| Alternative Benefits | | 0% |
| Health Account | | 0% |
| Premium Prepayment | | 0% |
| Total: | | 100% |
| NOTE: | | |
| Total must add to 100% between Fixed Residual Premium and Excess Premium Allocation for Optional Benefit Suspension Features | | |

Suspendable Plan X  ⟵ 500

State 1 – Area 1 ⟵ 502
(Rate A)

| Age | Single Male | Single Female | Couple** | Male & Children) | Female & Children) | Family** |
|---|---|---|---|---|---|---|
| 0 | $323 | $323 | N/A | N/A | N/A | N/A |
| 1 | $194 | $194 | N/A | N/A | N/A | N/A |
| 2-18 | $129 | $129 | $258 | $367 | $367 | $516 |
| 19-24 | $138 | $169 | $305 | $394 | $427 | $563 |
| 25-29 | $155 | $167 | $342 | $413 | $445 | $600 |
| 30-34 | $161 | $210 | $391 | $439 | $468 | $649 |
| 35-39 | $212 | $236 | $448 | $470 | $494 | $706 |
| 40-44 | $252 | $275 | $527 | $510 | $533 | $785 |
| 45-49 | $311 | $294 | $605 | $569 | $552 | $863 |
| 50-54 | $401 | $332 | $733 | $659 | $590 | $991 |
| 55-59 | $521 | $400 | $921 | $779 | $658 | $1,179 |
| 60-64 | $723 | $508 | $1,241 | $991 | $766 | $1,499 |
| 65+*** | $763 | $569 | $1,352 | $1,041 | $827 | $1,610 |

⟵ 504

Rate A = Lowest Risk Rate
Rate B = Rate A + (Rate A * 0.25)  ⟵ 506
Rate C = Rate A + (Rate A * 0.5)  ⟵ 508

FIGURE 5

| Fixed Residual Premium: | 10% |
|---|---|
| Optional Benefit Suspension Feature | Select Excess Premium Allocation (after payment of fixed residual premium above) |
| Premium Reduction | 90% |
| Alternative Benefits | 0% |
| Health Account | 0% |
| Premium Prepayment | 0% |
| Total: | 100% |
| NOTE: | |
| Total must add to 100% between Fixed Residual Premium and Excess Premium Allocation for Optional Benefit Suspension Features | |

FIGURE 7

| Fixed Residual Premium: | | 10% |
|---|---|---|
| Optional Benefit Suspension Feature | Select Excess Premium Allocation (after payment of fixed residual premium above) | |
| Premium Reduction | | 30% |
| Alternative Benefits | | 20% |
| Health Account | | 20% |
| Premium Prepayment | | 20% |
| Total: | | 100% |
| NOTE: | | |
| Total must add to 100% between Fixed Residual Premium and Excess Premium Allocation for Optional Benefit Suspension Features | | |

FIGURE 8

SYSTEM AND METHOD FOR OFFERING AND GUARANTEEING RENEWAL OF SUSPENDABLE HEALTHCARE BENEFITS

This invention relates generally to the field of insurance and more specifically to the area of healthcare coverage plans.

BACKGROUND OF THE INVENTION

In a world of increasing healthcare costs, availability of affordable health insurance is a driving factor in decisions affecting a wide spectrum of issues—from quality of life, to personal finances and family planning. The basic principles of health insurance have long remained the same—a person subscribes to a health insurance policy, often through his employer, and pays the insurance company a premium in exchange for coverage under the policy's terms. In addition to receiving some type of assurance that their healthcare services will be paid for, subscribers additionally typically receive the benefit of a lower price for those services, as participating healthcare providers generally are under contract with the insurance company to limit the maximum amount the insurance company will pay the provider for particular services rendered.

Although the basic principles of health insurance may not have changed, increasing costs of healthcare have created opportunities for many variations and nuances beyond the basic principles in order to more adequately serve the needs of health insurance consumers. These variations include different types of plans, such as POS, PPO, and HMO, all geared toward providing various deductible limits, co-payment amounts, coinsurance rates, and specific benefit limits. Moreover, the options for purchasing health insurance coverage are also expanding. In particular, as the nature of employment and employee-based benefits is changing, more consumers are looking for individual health insurance options to protect themselves and their families.

Continuity and affordability of healthcare coverage remains central to all healthcare consumers. This is particularly the case for individuals that find themselves between jobs or in employment settings without group healthcare coverage. Similarly, healthcare consumers that are planning an early retirement face the prospect of losing group coverage upon retirement and need to arrange for alternate coverage prior to becoming eligible for an assisted healthcare plan, such as Medicare. Individual health coverage options available to consumers to fill these gaps typically are subject to some form of underwriting, which subjects the consumer to a possibility of increased premiums or denial of coverage in the event the consumer is in poor health or has been diagnosed with a serious health condition at the time coverage is sought.

BRIEF SUMMARY OF THE INVENTION

Embodiments of the invention are used to provide a suspendable health insurance plan (SHIP) allowing consumers to be underwritten for coverage based on current health status and having a benefit suspension feature for suspending at least one of a healthcare consumer's benefits under the plan, where renewal of the at least one suspended benefit is guaranteed by the health plan organization according to the underwriting status determined during the initial underwriting process. In one embodiment, the suspendable plan is an individual healthcare coverage plan. The plan can be offered in a variety of benefit designs comparable to the range of health benefits available with conventional plans.

In an embodiment, when a healthcare consumer purchases a suspendable plan while having group coverage, which is typically during periods of employment, the consumer is able to suspend the benefits under the plan until he or she is no longer covered by a group healthcare plan, which may be at early retirement, for example. Thus, upon early retirement, the consumer can activate the suspendable plan until becoming eligible for Medicare. Alternatively or in addition, when the terms of the group plan are undesirable, the consumer may elect not to be covered by the group plan and elect to renew the benefits under the suspendable plan. Similarly, a healthcare consumer can buy a suspendable plan while not covered by a group plan. Typically, such consumer is a younger worker without access to group coverage or a consumer in an employment setting where group coverage is not available. In this case, as consumer's employment status changes, he or she can maintain the suspendable plan as a personal safety net, suspending the benefits when group coverage is available and renewing the benefits under the plan between jobs or in employment settings without group coverage. The health plan organization, in turn, guarantees renewal of one or more benefits suspended under the plan throughout the life of the policy at the underwriting status determined when the consumer initially applied for suspendable coverage and, most likely, was in better health.

In an embodiment, the renewal is guaranteed upon the policyholder meeting predetermined conditions. The predetermined conditions for renewal are necessary to assure that the plan is maintained on a continuous basis and that the decision to stop the suspension is based on an external factor, e.g., termination of group eligibility at retirement, rather than an adverse health event.

When the consumer chooses to suspend one or more benefits under the plan, the healthcare plan organization reduces the plan premium to a residual premium reflecting the risk associated with providing a renewal guarantee. Hence, after establishing the full plan premium, the health plan organization determines the residual premium, which is a percentage of the full premium, that the consumer continues to pay during the period of benefit suspension. Each year's residual premium is established primarily using a difference between an estimated percent increase in benefits to be claimed in a given year by a new healthcare consumer and the percent increase in the amount of benefits claimed in the corresponding year by similar underwritten consumers. The consumer must pay at least the residual premium during the benefit suspension period in order for the health plan organization to guarantee renewal of the policy at the initial underwriting status.

In embodiments, the benefits under the plan are suspended according to one or more of a plurality of benefit suspension features. In one embodiment, upon benefit suspension, the consumer simply receives a substantial premium reduction from the full premium. Another embodiment includes an option of receiving alternative benefits, e.g., dental benefits, term life insurance, when the SHIP health benefits are suspended. In yet another embodiment, the benefit suspension features include an option of funding a health savings account (HSA) or having the surplus premium accumulated in a spending account within the policy to cover deductible or co-insurance obligations during renewal periods. In a further embodiment, the consumer is presented with an option to allocate some or all of the excess premium during the period of suspension toward prepayment of future premiums payable when one or more of the suspended benefits under the policy are reactivated. This may be an attractive option for those consumers wishing to finance their suspendable coverage insofar as possible during periods of employment. The amount of the optional benefits, such as alternative benefits, an HSA account, or premium prepayment above is determined by the portion of the full SHIP plan premium the consumer continues to pay, less the portion of the premium associated with a renewal guarantee (i.e., the residual premium). The excess premium available after payment of the residual premium may be used to combine any of the optional benefit suspension features.

In one aspect of the invention, a method is provided for a health plan organization to guarantee renewal of a healthcare coverage plan, the method comprising determining a healthcare consumer's underwriting status, enrolling the consumer in the healthcare coverage plan for providing healthcare benefits to the consumer, the healthcare coverage plan comprising a benefit suspension feature for suspending at least one of the consumer's benefits under the plan, suspending the at least one of the consumer's benefits according to the benefit suspension feature, and guaranteeing renewal of the at least one suspended benefit according to the determined underwriting status.

In another aspect of the invention, a system is provided for determining an underwriting status of a healthcare consumer and guaranteeing renewal of a healthcare coverage plan for the consumer, the system comprising a health information questionnaire for collecting health information from the consumer, a database of medical claim history, and a computer readable medium having thereon instructions for determining the consumer's underwriting status based at least on the health information questionnaire and the database of medical claim history, wherein the healthcare coverage plan comprises a benefit suspension feature for suspending at least one of the consumer's benefits under the plan, and wherein renewal of the at least one benefit is guaranteed according to the underwriting status.

In still another aspect of the invention, a method is provided for reducing a healthcare coverage plan premium, wherein a reduced premium reflects risk associated with guaranteeing renewal of at least one benefit under a healthcare coverage plan, the plan comprising a benefit suspension feature for suspending the at least one benefit, the method comprising determining an initial premium for a new healthcare consumer assuming a fully active healthcare coverage plan, estimating a percent increase in a value of benefits the new healthcare consumer is likely to claim within a year, determining a percent increase in a value of benefits claimed by existing similar healthcare consumers within the year, and reducing the initial premium to a residual percentage based at least in part on a difference between the estimated and the determined percent increase values.

BRIEF DESCRIPTION OF THE DRAWINGS

While the appended claims set forth the features of the present invention with particularity, the invention and its advantages are best understood from the following detailed description taken in conjunction with the accompanying drawings, of which:

FIG. 5 is a chart illustrating a rate table for determining the healthcare consumer's premium rate when all the benefits under a suspendable plan are active, in accordance with an embodiment of the invention;

FIGS. 7, 8 are charts illustrating various allocation of excess premium among a plurality of benefit suspension options, in accordance with embodiments of the invention.

DETAILED DESCRIPTION OF THE INVENTION

The following examples further illustrate the invention but, of course, should not be construed as in any way limiting its scope.

Figure 1:
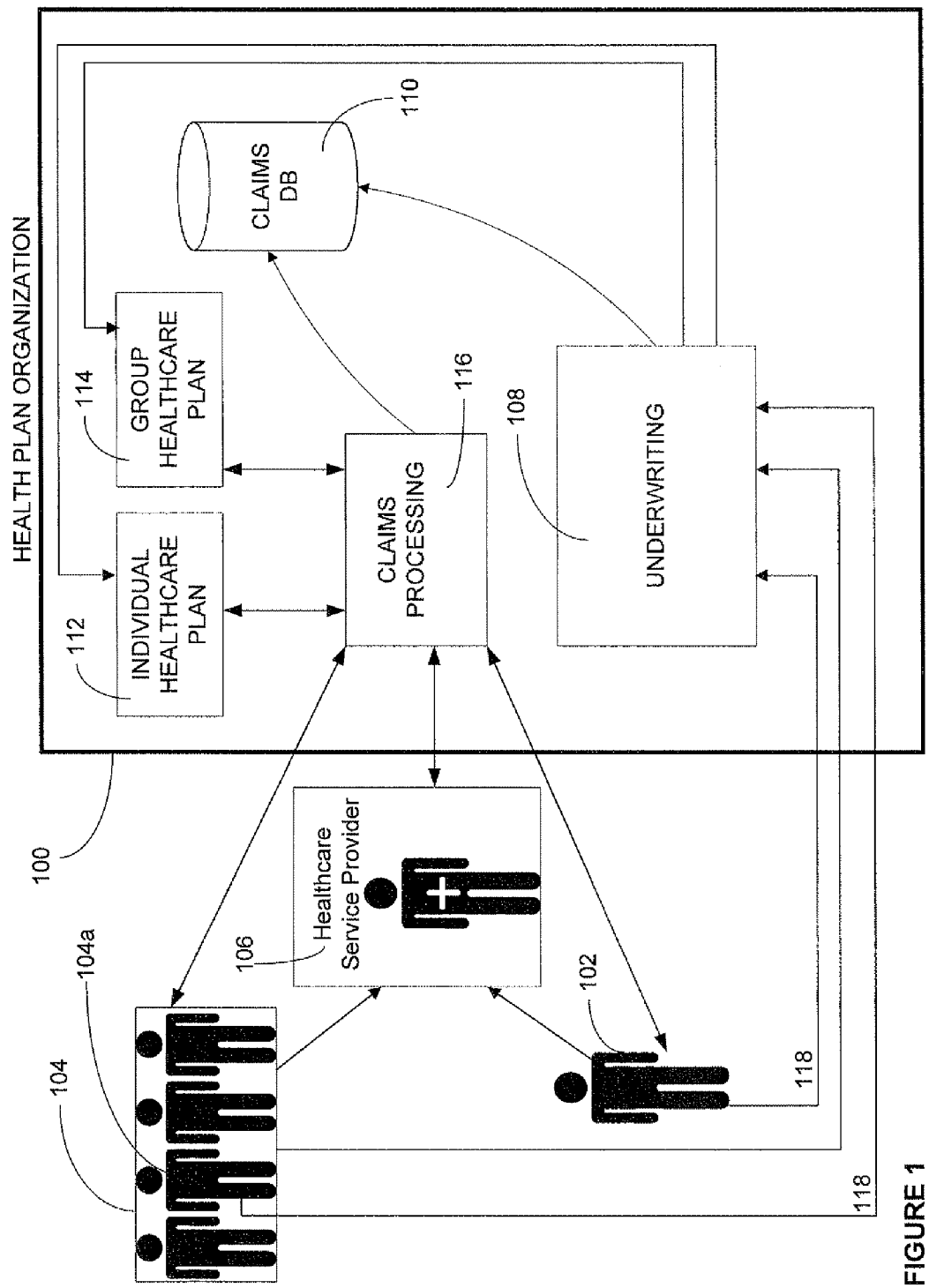
FIG. 1 is a general overview of an environment, wherein a health plan organization interacts with a healthcare consumer, a group of healthcare consumers, and a healthcare service provider for underwriting and issuing group and individual healthcare plans, as well as for processing medical services claims, as contemplated by an embodiment of the present invention.

Turning to FIG. 1, an implementation of a system contemplated by an embodiment of the invention is shown with reference to an overall health plan organization environment. In one embodiment, the health plan organization (HPO) 100 is a health insurance company that underwrites individual and group healthcare coverage plans 112, 114. When an individual healthcare consumer 102 wishes to obtain healthcare coverage, the health plan organization 100 relays the underwriting information 118 from the healthcare consumer 102 to the underwriting team 108. The underwriting information 118 includes consumer's address, age, sex, current health status, past health history, as well as health risk factors (as permitted under applicable regulation) such as smoking habits, family health history, and dangerous activities, for example. By analyzing the underwriting information 118, in conjunction with the medical claim history information stored in the claims database 110, the underwriting team 108 evaluates the risk involved in providing a health care coverage policy for the consumer 102. The risk is translated into an underwriting status, which, in turn determines whether a consumer is insurable and establishes a healthcare plan premium, as discussed in further detail below in FIGS. 4 and 5. Upon obtaining healthcare services from a healthcare service provider 106, either the consumer 102 or the healthcare service provider 106 submits a claim for payment to the claims processing team 116 of the health plan organization 100. The claims processing team 116, upon storing the claim information in the claims database 110, analyzes the claim with respect to the terms and conditions stipulated in the individual healthcare plan 112. If the terms and conditions of the healthcare plan 112 are met, the claim processing team 116 issues a payment to the healthcare service provider 106 or to the consumer 102. Typically, the healthcare service provider 106 is under contract with the health plan organization 100 to limit the service charges to the consumer 102 when the consumer 102 obtains a healthcare coverage plan 112 from the health plan organization 100. This lowers the consumer's out-of-pocket costs and the health plan organization 100 benefit payout costs, while increasing the volume of consumers 102 referred to the healthcare service provider 106.

Alternatively, a group of healthcare consumers 104 obtains a group healthcare plan 114. Group of healthcare consumers 104 may be associated with an employer or any other collection of individuals which qualifies for group coverage under the health plan organization's 100 underwriting guidelines. While the group 104 also undergoes underwriting 108, the underwriting status of the group 104 is less influenced by a personal health status of a given group member because underwriting the group 104 involves analyzing the overall composition of the group to ensure that the total risk is not excessive. This makes it easier for the healthcare consumer 104a to obtain healthcare coverage as a member of the group 104. Conversely, when the consumer 104a is no longer covered by a group plan 114, obtaining healthcare coverage may become more difficult because consumer's 104a personal health issues heavily factor in the underwriting status for obtaining individual healthcare coverage.

To that end, a suspendable health insurance plan (SHIP) is provided having a benefit suspension feature for suspending at least one of a healthcare consumer's benefits under the plan, where the renewal of the at least one suspended benefit is guaranteed by the health plan organization according to the underwriting status determined during the initial underwriting process. In one embodiment, the individual healthcare plan 112 is a suspendable healthcare plan. Thus, when a healthcare consumer 104a purchases a suspendable individual healthcare plan 112 while having group coverage 114, which is typically during periods of employment, the consumer 104a is able to suspend the benefits under the suspendable individual healthcare plan 112 until he or she is no longer covered by a group healthcare plan 114, which may be at early retirement, for example. Thus, upon early retirement, the consumer 104a can activate the suspendable plan 112 until becoming eligible for Medicare. Alternatively or in addition, when the terms of the group plan 114 are undesirable, the consumer 104a may elect not to be covered by the group plan 114 and elect to renew the benefits under the suspendable plan 112. The health plan organization 100, in turn, guarantees renewal of one or more benefits suspended under the plan 112 throughout the life of the policy at the underwriting status determined when the consumer initially applied for suspendable coverage and, most likely, was in better health. In this embodiment, the suspendable policy or plan 112 is of a predetermined duration, which is typically until the consumer reaches the age of 65. In an embodiment, the renewal is guaranteed upon the policyholder meeting predetermined conditions, such as, for example, within 60 days from losing group coverage or up to becoming eligible for Medicare. The predetermined conditions for renewal are necessary to reduce the risk for the health plan organization 100 that renewal is triggered only upon the occurrence of an adverse health event, such as when the consumer loses group coverage, waits an indeterminate period of time prior to activating the suspended benefits, gets diagnosed with a serious illness in the interim, and only then activates coverage.

Similarly, an individual healthcare consumer 102 can buy the suspendable plan 112 while not covered by a group plan. Typically, a healthcare consumer 102 is a younger worker without access to group coverage or a consumer in an employment setting where group coverage is not available. As consumer's 102 employment status changes, he or she can maintain the suspendable plan 112 as a personal safety net, suspending the benefits when group coverage is available and renewing the benefits under the suspendable plan 112 between jobs or in employment settings without group coverage. Therefore, suspendable coverage plans provide continuity of healthcare coverage protection for the consumers 102, 104a under circumstances which result in unavailability or undesirability of group coverage. Additionally, suspendable healthcare coverage plan 112 may qualify as prior creditable coverage for purposes of avoiding a benefit waiting period imposed by a subsequent employer having group coverage.

Suspendable healthcare coverage plan 112 can be offered in a variety of benefit designs comparable to the range of health benefits available with conventional plans. In one embodiment, the healthcare plan 112 includes comprehensive hospital and physician (major medical) coverage, while being subject to a high annual deductible that makes the coverage more affordable and/or permits continued funding of an Health Savings Account (HSA), a Flexible Spending Account (FSA), or the like. In other embodiments, the plan 112 is a limited benefit plan. For example, the plan 112 may offer specific benefits designed to protect against critical illnesses. Alternatively, the plan 112 may offer more comprehensive benefits that are subject to an annual benefits cap. In yet another embodiment, the plan 112 includes benefits for prescription drugs, dental care, vision care and other ancillary care. In a further embodiment, the plan 112 is offered with a conversion option to a Medicare Advantage or Medicare supplement plan after the consumer 102, 104a reaches the Medicare eligibility age, which is currently 65 years old. In this case, to ease the transition, the plan 112 is designed to mirror the benefits of these Medicare conversion options.

Figure 2:
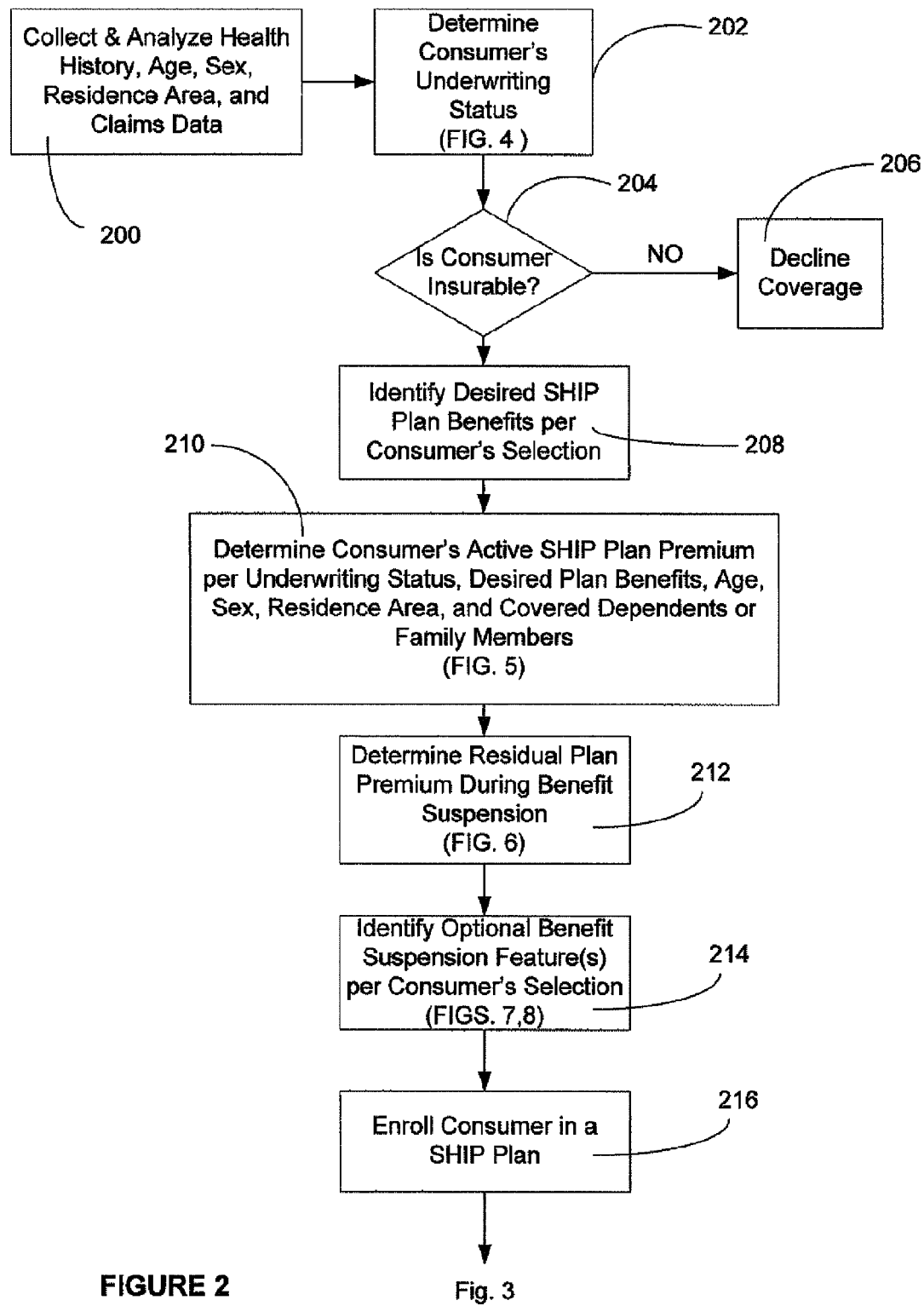
FIGS. 2, 3 are flowcharts illustrating a method of guaranteeing renewal of benefits under a suspendable healthcare coverage plan and according to a predetermined underwriting status, in accordance with an embodiment of the invention.
Figure 3:
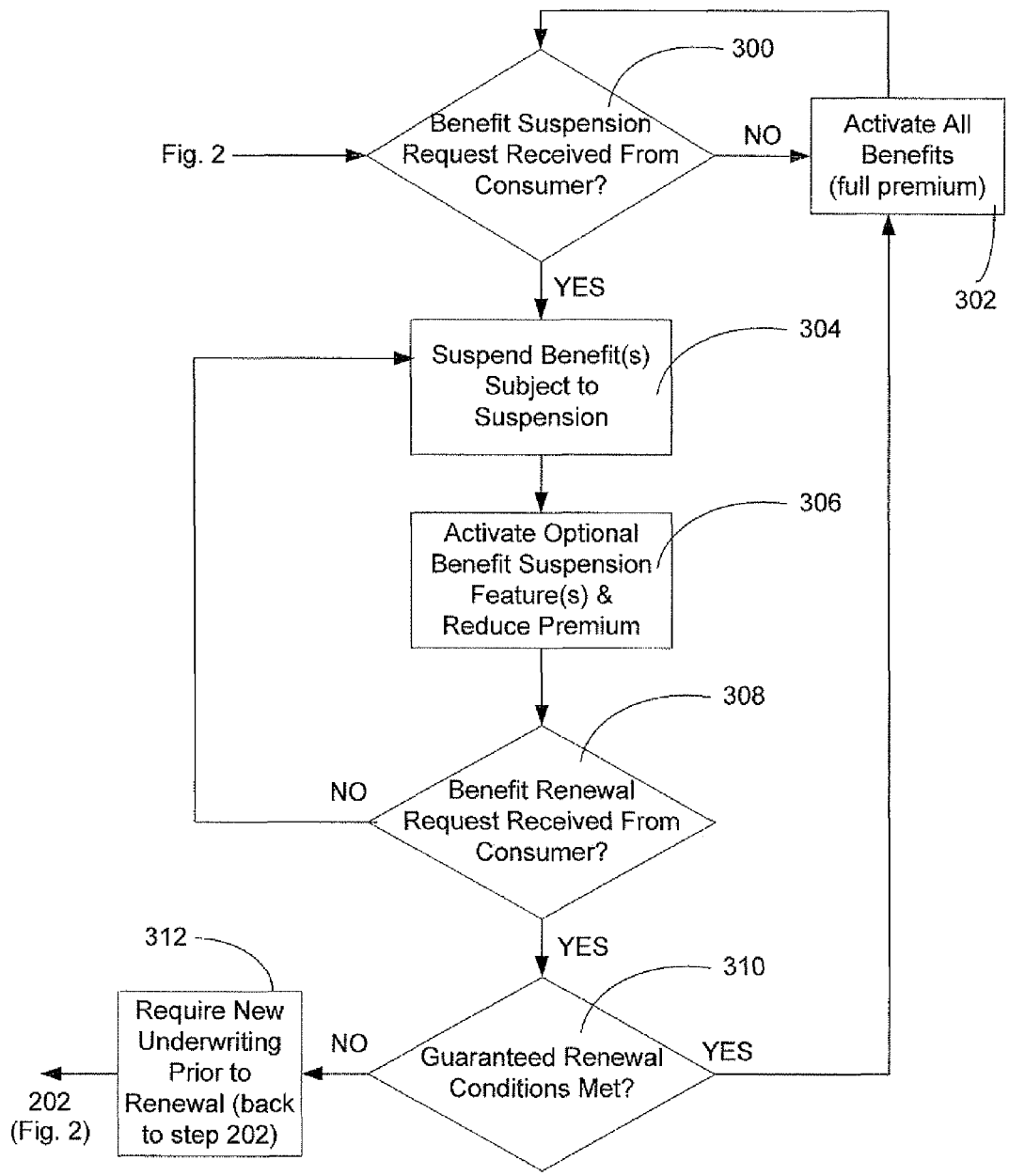

Turning to FIGS. 2, 3 a method is shown for a health plan organization to guarantee renewal of a suspendable healthcare coverage plan, in accordance with an embodiment of the invention. In step 200, the health plan organization 100 collects and analyzes the consumer's 102, 104a health, age, sex, and geographic area information, as well as claims data for existing consumers in the same demographic category, to determine, in step 202, the consumer's 102, 104a underwriting status (FIG. 4) for purposes of determining in step 204 whether the consumer is insurable. If the consumer is insurable, the health plan organization 100 determines the consumer's suspendable plan 112 premium.

Figure 4:
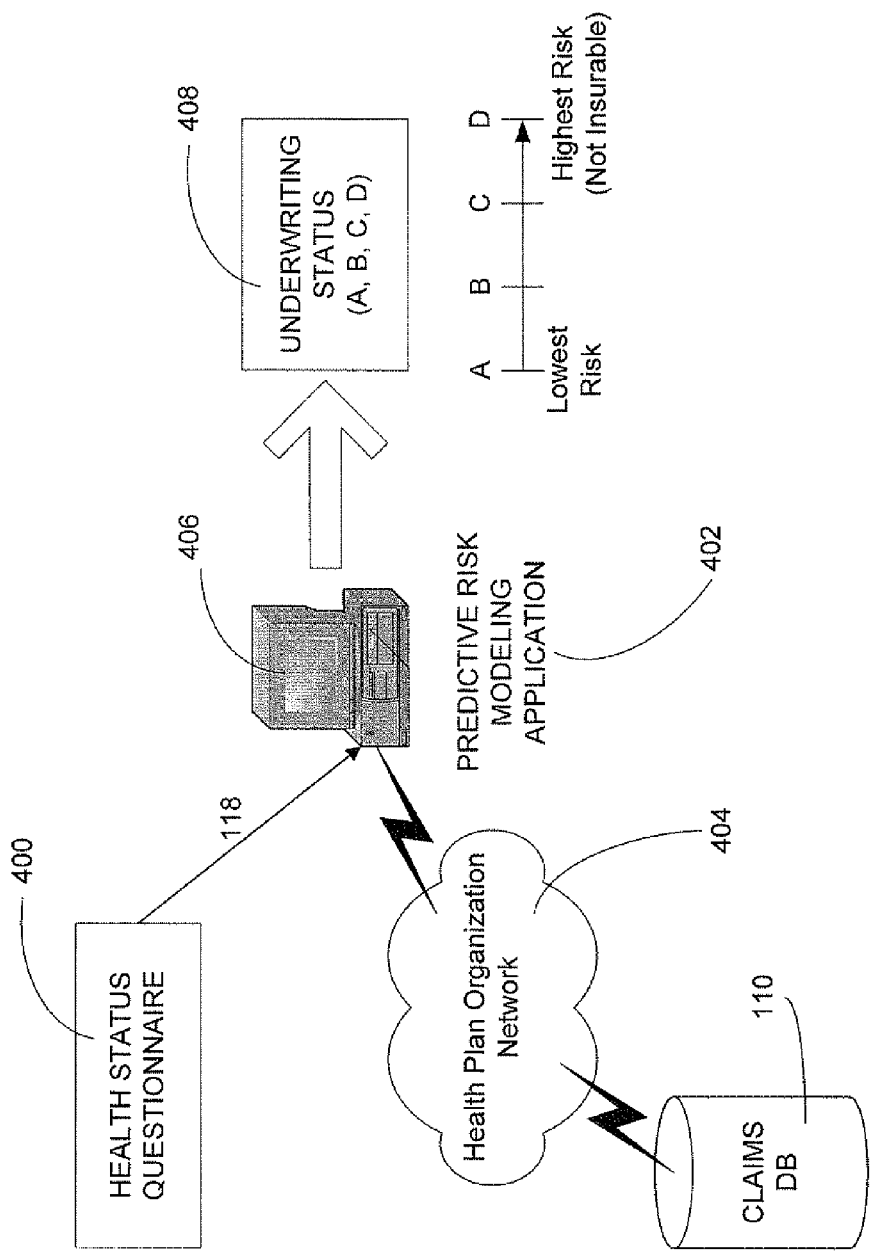
FIG. 4 is a diagram illustrating a system for determining a healthcare consumer's underwriting status, in accordance with an embodiment of the invention.

To determine the consumer's underwriting status, in an embodiment of the invention, a system such as the one shown in FIG. 4 is preferably employed. Specifically, a health status questionnaire 400 is provided to the consumer 102, 104a as part of the application process for suspendable coverage plan 112. In an embodiment, the health status questionnaire 400 is a hard copy health insurance application. Other embodiments include presenting the questionnaire 400 over a computing device, such as via a secured web browser interface residing on a computer for example, and submitting the collected information via a network, such as the Internet, to the health plan organization 100. The health status questionnaire 400 is geared toward collecting the underwriting information 118, which comprises consumer's address, age, sex, current health status, past health history, and health risk factors such as smoking habits, family health history, and dangerous activities. In addition to the underwriting information 118 specific to the new consumer 102, 104a, the health plan organization 100 also collects historical medical claim data on its previously underwritten consumers and stores it within the claims database 110. Once collected, the underwriting information 118 and the medical claim history pertaining to previously underwritten consumers within the same demographic category as the consumer 102, 104a are used to determine, based on actuarial calculations, an appropriate rate level for individuals with comparable demographic and health status risks. This premium rate, along with comparable rates for other demographic and health risk classifications, may be embodied in a rate table established by the health plan organization 100 for the particular insurance product. Alternatively, the collective underwriting and claim information collected may be included among a plurality of inputs to predictive risk modeling application 402 residing on a computing device 406, and this predictive modeling tool 402 may be used to calculate specific premium rates by demographic and health risk classification. In the illustrated embodiment, the claims database 110 is connected to the computing device 406 via a health plan organization network 404. Other embodiments include connecting the claims database 110 to the computing device 406 via another network, such as the Internet. Alternatively, the claims database 110 may be part of the computing device 406. Similarly, the results of the health status questionnaire 400 may serve as direct input to the predictive risk modeling application 402, or stored in another database for future processing.

The health insurance organization 100 analyzes the consumer's 102, 104a underwriting information 118, in conjunction with criteria derived from historical claim data from the claims database 110, to come up with the consumer's 102, 104a underwriting status 408. Preferably, the underwriting status 408 is divided into a plurality of risk categories. For example, in one embodiment, the risk categories include A, B, C, and D risk ratings. The risk categories A-D represent degrees of risk, from lowest to highest, associated with providing the consumer 102, 104a with suspendable healthcare coverage plan 112. In this illustration, risk category A corresponds to the lowest risk, while risk category D represents the highest risk and may correspond to an uninsurable consumer for whom healthcare coverage may be denied. For example, a 20-year-old non-smoker without any health issues is likely to be placed in the lowest "A" risk category, while a 20-year-old diabetic may be a higher insurance risk, which may correspond to a "B" risk rating. Correspondingly, a 64-year-old smoker with diabetes and a history of serious heart disease may be placed within a "C" or "D" risk rating.

Referring to FIG. 2, if the consumer's underwriting status corresponds to the highest "D" risk rating, the suspendable healthcare plan coverage is declined in step 206. If, however, the underwriting status falls within any insurable risk category (e.g., A-C), the healthcare plan organization 100, in step 208, identifies the desired SHIP benefit design selected by the consumer 102, 104a when applying for coverage.

In step 210, to determine the plan rate payable when all the benefits under the SHIP plan 112 are activated, the health plan organization 100 correlates the consumer's age, sex, and residence area demographics with any covered dependents or family members within a rate table corresponding to a particular plan benefit design selected by the consumer 102, 104a, and the consumer's previously determined underwriting status. Base rates within a rate table are preferably established for each residential area or "market" and age/sex basis based on historical experience in such market and based on predicted cost trends. Specifically, as illustrated in FIG. 5, an exemplary rate table 504 corresponding to plan 500 selected by the consumer 102, 104a is used to determine the active plan rate corresponding to a consumer with an "A" (lowest risk) underwriting status and residing in an area or market 502. Once the "A" underwriting status is determined, the health plan organization 100 uses the rate formulas 506, 508 to adjust the applicable premium to the underwriting status specific to the consumer 102, 104a, as determined in connection with FIG. 4 above. For example, a 20-year-old single male consumer applying for a suspendable plan with a plan benefit design 500, and residing in residential area 502, would pay a monthly premium of $136 for a fully active plan if such consumer receives an "A" underwriting status. For the same consumer with a "B" underwriting status, however, the premium is adjusted using the corresponding "Rate B" formula 506 to reflect the higher risk.

Figure 6:
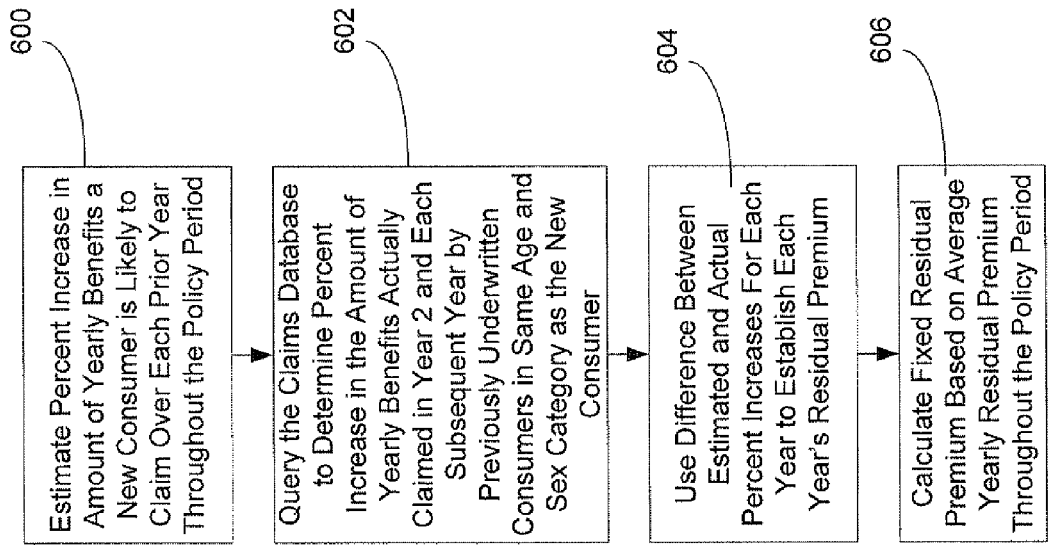
FIG. 6 is a flowchart illustrating a method of calculating a residual premium payable during benefit suspension, in accordance with an embodiment of the invention.

When the consumer 102, 104a chooses to suspend one or more benefits under the plan 112, the healthcare plan organization 100 will reduce the plan premium to a residual premium reflecting the risk associated with providing a renewal guarantee. Hence, in FIG. 2, after establishing the full plan premium, the health plan organization, in step 212, determines the residual premium that the consumer 102, 104a will pay during the period of benefit suspension. As seen in more detail in FIG. 6, one approach the health plan organization 100 may take to determine the residual premium is to calculate the expected increase in claim costs due to deterioration in health status over a period of years following initial underwriting. Under this approach, the health plan organization 100 may estimate, in steps 600-604, a percent increase in the amount of yearly benefits for underwritten individuals in year 2 and subsequent years of their coverage compared to the "baseline" increase for newly-underwritten individuals each year. This incremental difference would be used as a primary factor, at step 604, to determine the residual premium payable under the SHIP to maintain the coverage while benefits are suspended. Other relevant factors may include taking into account such variables as unusual claim activity within the sample, market-driven effects on pricing of new consumer plans, sales and administrative costs, as well as other factors having an effect on the accuracy of the calculation. In one embodiment, the residual premium trend is smoothed out over a number of years to increase the credibility of the calculation. For example, if for a given year the estimated "baseline" percent increase in yearly benefit claims over a prior year is 5% and the actual percent increase observed for previously underwritten consumers in the same age/sex category is 12%, the difference in these rates, as well as other factors noted above, would be used to calculate the residual premium for such year. The consumer 102, 104a would be obliged to pay at percentage of the base SHIP premium determined from this calculation during the benefit suspension period in order for the HPO 100 to guarantee renewal of the policy at the initial underwriting status. In one embodiment, in order to provide a fixed residual rate, the HPO 100 calculates an average value of yearly residual premiums throughout the policy period, as seen in step 606. Because the residual premium will be determined for customers at various age groups and because suspension periods may last longer for consumers who purchase coverage at a younger age, the residual premium percentages may vary based on applicant age at the time the SHIP policy is purchased. For example, a consumer within a 60-65 age group may pay a fixed (averaged) 8% of the annual premium during benefit suspension, while an individual within a 50-55 age group may pay a fixed 10% of the annual premium for a comparable SHIP policy. In other embodiments, plans that are subject to suspension of benefits for more than five years have a stepped variable residual premium, such as 6% of the full premium for the first five years, and 8% of the full premium for subsequent years. It should be noted that at plan inception there may not be enough data regarding actual claim experience of previously-underwritten SHIP consumers. In this case, the HPO 100 may use claim experience of consumers underwritten for another healthcare plan in establishing the residual rate described above. Over time, however, as the HPO 100 develops sufficient credible experience within the SHIP plans themselves, that actual experience would be used, in whole or in combination with methods like the one described above, to determine the residual premium rates for the plans.

In embodiments, the benefits under the plan 112 are suspended according to one or more of a plurality of benefit suspension features. In one embodiment, upon benefit suspension, the consumer 102, 104a simply receives a substantial premium reduction from the full premium, such as a 90% reduction, for example. The remaining 10% is a residual premium, calculated as described in connection with FIG. 6 above, reflecting the risk inherent in a favorable renewal guarantee using the underwriting status determined when the consumer first applied for a suspendable policy. In this embodiment, the consumer 102, 104a continues to have access to other services offered by the HPO 100, such as on-line health information, a personal data record, and access to service discounts, for example. Another embodiment includes an option of receiving alternative benefits when the SHIP health benefits are suspended. The alternative benefits may include critical illness coverage, enhanced drug or dental benefits, or term life insurance, disability insurance or AD&D coverage. In yet another embodiment, the benefit suspension features include an option of funding a health savings account (HSA) or a benefit account within the plan wherein the amount of funding is equal to a specified percentage of a difference between premiums paid and benefits claimed during a period when the consumer was subject to group coverage. The accumulated HSA or benefit account can also be used in conjunction with the benefits under the plan 112 when the policy is reactivated. The funds accumulated in the account are used for payment of deductibles, co-insurance amounts, or other non-covered medical expenses. In an embodiment, the accumulation of funds in an account could be coupled with a return of premium in the event the policyholder dies or is otherwise unable to take advantage of the benefits under the suspendable plan 112 post-retirement. In yet another embodiment, the consumer is presented with an option to allocate some or all of the excess premium during the period of suspension toward prepayment of future premiums payable when one or more of the suspended benefits under the policy 112 are reactivated. This may be an attractive option for those consumers 102, 104a wishing to finance their suspendable coverage insofar as possible during periods of employment. It should be further noted that the amount of the optional benefits, such as alternative benefits, an HSA account, or premium prepayment above is determined by the portion of the full SHIP plan premium the consumer continues to pay, less the portion of the premium associated with a renewal guarantee (i.e., the residual premium).

Additionally, the excess premium available after payment of the residual premium may be used to combine any of the optional benefit suspension features above. That is, instead of choosing to only pay the residual premium during benefit suspension and, therefore allocate all excess premium toward a premium reduction, the consumer 102, 104a may elect to allocate none or only part of the excess premium toward a premium reduction, while distributing the remainder of the excess premium toward other benefit suspension features above. In one embodiment, the combination is determined by the consumer 102, 104a within limits specified by the policy. This principle is illustrated in more detail in FIGS. 7 and 8. In FIGS. 7 and 8 the consumer 102, 104a is provided with a fixed residual premium percentage 700, 800 and is able to allocate excess premium, representing the difference between the full premium and the residual premium, among any of the optional benefit suspension features above. Therefore, in the embodiment illustrated in FIG. 7, the consumer chooses to allocate all excess premium toward receiving a substantial premium reduction 702, which in this example is a 90% reduction in premium. Alternatively, in FIG. 8, the consumer elects to distribute the excess premium among getting a 30% premium reduction 802, paying 20% of the full premium for alternative benefits 804, paying another 20% of the full premium to fund an HSA account 806, and allocating the remaining 20% of the full premium toward prepayment 808 of future premium payable when all the benefits are reactivated.

Next, returning to FIG. 2, based on consumer's allocation of excess premium available after payment of the residual, the HPO 100 identifies one or more optional benefit suspension features in step 214 and enrolls 216 the consumer in a suspendable healthcare plan. As shown in FIG. 3, unless the HPO 100 receives 300 a request from the consumer to suspend one or more benefits subject to suspension under the plan 112, the HPO 100 activates 302 all benefits and charges the full active premium. Preferably, during enrollment, the consumer is able to make a selection directing the HPO 100 to immediately suspend one or more benefits under the plan. In this case, the benefits are suspended immediately upon enrollment. Alternatively, the consumer is able to activate the plan benefits upon enrollment and submit a request for benefit suspension at a later point in time, such as when group coverage becomes available, for example. If the benefit suspension request is received, the HPO 100 suspends 304 benefits subject to suspension per applicable plan terms. Upon suspending one or more benefits under the plan 112, the HPO 100 activates 306 the optional benefit suspension features previously selected by the consumer and reduces the premium to a residual premium, determined in step 212 (FIG. 2), combined with any excess premium allocated among one or more optional benefit suspension features discussed above in connection with FIGS. 7, 8. If the HPO 100 receives 308 a request from the consumer 102, 104a to renew the suspended benefits, the HPO 100 checks 310 whether the consumer meets the applicable conditions for guaranteed renewal with the consumer's predetermined underwriting status. As discussed above, the conditions may include becoming eligible for Medicare, an age limit and/or a specified time limit after loosing group coverage eligibility, among others. If the consumer does not meet guaranteed renewal conditions, the HPO 100 may require 312 the consumer 102, 104a to go through another underwriting process prior to renewal of benefits. In this case, the consumer 102, 104a runs the risk of falling within a higher risk and premium category, or becoming uninsurable due to a change in the health status. If, however, the consumer 102, 104a meets the conditions for a guaranteed renewal with the initial underwriting status, the HPO 100 reactivates 302 all benefits under the plan without changing the consumer's underwriting status and corresponding risk/rate category.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for a health plan organization to guarantee renewal of a healthcare coverage plan, the method comprising:
   determining, via an underwriting risk modeling computing device, a healthcare consumer's underwriting status;
   providing an electronic interface for enrolling the consumer in the healthcare coverage plan that provides healthcare benefits to the consumer in connection with payment of a first healthcare plan premium, the healthcare coverage plan comprising a benefit suspension feature for suspending at least one of the consumer's benefits under the plan;
   processing user input from the electronic interface for suspending the at least one of the consumer's benefits according to the benefit suspension feature, wherein the healthcare coverage plan guarantees renewal of the at least one suspended benefit according to the initially determined underwriting status in connection with payment of a second healthcare plan premium which comprises a reduction to a residual percentage of the first premium, the second healthcare plan premium reflecting a risk associated with guaranteeing renewal of the at least one suspended benefit;
   calculating the reduction to the residual percentage of the first premium based at least in part on a difference between estimated and determined percent increases in a value of claimed benefits within a predetermined time period; and
   processing user input from the electronic interface reflecting the healthcare consumer's allocation of an excess premium comprising a difference between the first and second healthcare plan premiums among one or more of a plurality of excess premium allocation options.

2. The method of claim 1 wherein the renewal according to the underwriting status is guaranteed upon one or more predetermined conditions.

3. The method of claim 2 wherein the one or more predetermined conditions is at least one of a predetermined time period, an age limit.

4. The method of claim 1 further comprising providing alternative benefits when the at least one benefit is suspended.

5. The method of claim 1 further comprising accumulating a healthcare account for payment of non-covered healthcare expenses incurred when the at least one suspended benefit is renewed.

6. The method of claim 1 further comprising prepaying of renewal premium when the at least one benefit is suspended.

7. The method of claim 1 wherein the excess premium allocation options are selected from the group consisting of a premium reduction, an alternative benefit selection, funding of a healthcare account, and a prepayment of a future premium payable when the at least one benefit is renewed.

8. A system for determining an underwriting status of a healthcare consumer and guaranteeing renewal of at least one benefit under a healthcare coverage plan that provides healthcare benefits to the consumer in connection with payment of a first healthcare plan premium, the system comprising:
   a health information questionnaire for collecting health information from the consumer;
   a database of medical claim history; and
   a computer readable medium having thereon instructions for determining the consumer's underwriting status based at least on the health information questionnaire and the database of medical claim history, wherein the healthcare coverage plan comprises a benefit suspension feature for suspending the at least one of the consumer's benefits under the plan, and wherein renewal of the at least one benefit is guaranteed according to the initially determined underwriting status in connection with payment of a second healthcare plan premium which comprises a reduction to a residual percentage of the first healthcare plan premium, the second healthcare plan premium reflecting a risk associated with guaranteeing renewal of the at least one suspended benefit; and
   the computer readable medium having thereon further instructions for: (a) calculating the reduction to the residual percentage of the first premium based at least in part on a difference between estimated and determined percent increases in a value of claimed benefits within a redetermined time period, and (b) receiving the healthcare consumer's allocation of an excess premium comprising a difference between the first and second healthcare plan premiums among one or more of a plurality of excess premium allocation options.

9. The system of claim 8 further comprising a benefit renewal trigger for activating one or more benefits previously suspended with the benefit suspension feature, the benefit renewal trigger comprising one or both of:
   the healthcare consumer being unable to obtain a group healthcare coverage plan; and
   the health care consumer having chosen not to obtain a group healthcare coverage plan.

10. The system of claim 8 wherein the renewal according to the underwriting status is guaranteed upon one or more predetermined conditions.

11. The system of claim 8 wherein the healthcare coverage plan is of a predetermined duration.

12. The system of claim 8 wherein the healthcare coverage plan includes comprehensive hospital and physician coverage.

13. The system of claim 12 wherein the healthcare coverage plan further includes an annual benefits limit.

14. The system of claim 8 wherein the healthcare coverage plan is a limited benefit plan.

15. The system of claim 8 wherein the healthcare coverage plan includes ancillary care benefits.

16. The system of claim 8 wherein the excess premium allocation options are selected from the group consisting of a premium reduction, an alternative benefit selection, funding of a healthcare account, and prepayment of a future premium payable when the at least one benefit is renewed.

17. A method for reducing a healthcare coverage plan premium, wherein a reduced premium reflects risk associated with guaranteeing renewal of at least one benefit under a healthcare coverage plan, the plan comprising a benefit suspension feature for suspending the at least one benefit, the method comprising:

determining, via an underwriting risk modeling computing device, an initial premium for a new healthcare consumer assuming a fully active healthcare coverage plan;

estimating, via the underwriting risk modeling computing device, a percent increase in a value of benefits the new healthcare consumer is likely to claim within a predetermined time period;

querying a claims database for determining a percent increase in a value of benefits claimed by existing similar healthcare consumers within the predetermined time period;

calculating, via the underwriting risk modeling computing device, a reduction in the initial premium to a residual percentage based at least in part on a difference between the estimated and the determined percent increase values, wherein the reduced premium comprises the reduction in the initial premium to the residual percentage, the reduced premium being assessed when the at least one benefit is suspended; and receiving the healthcare consumer's allocation of an excess premium comprising a difference between the initial and reduced premiums among one or more of a plurality of excess premium allocation options.

18. The method of claim 17 wherein the reduced premium is fixed.

19. The method of claim 17 wherein the reduced premium varies based on duration of benefit suspension.

20. The method of claim 17 wherein the excess premium allocation options are selected from the group consisting of a premium reduction, an alternative benefit selection, funding of a healthcare account, and a prepayment of a future premium payable when the at least one benefit is renewed.

* * * * *